United States Patent
Tofovic et al.

(10) Patent No.: US 7,192,941 B2
(45) Date of Patent: Mar. 20, 2007

(54) ESTRADIOL METABOLITES FOR THE TREATMENT OF PULMONARY HYPERTENSION

(75) Inventors: Stevan P. Tofovic, Pittsburgh, PA (US); Edwin K. Jackson, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 76 days.

(21) Appl. No.: 10/781,850

(22) Filed: Feb. 20, 2004

(65) Prior Publication Data

US 2004/0209855 A1    Oct. 21, 2004

Related U.S. Application Data

(60) Provisional application No. 60/448,118, filed on Feb. 20, 2003.

(51) Int. Cl.
    *A61K 33/56*    (2006.01)
(52) U.S. Cl. .................... 514/171; 514/181; 514/182
(58) Field of Classification Search ................ 514/170, 514/172, 182, 171, 180, 181
    See application file for complete search history.

(56) References Cited

U.S. PATENT DOCUMENTS

| | | | |
|---|---|---|---|
| 5,736,154 A | 4/1998 | Fuisz | |
| 5,788,980 A | 8/1998 | Nabahi | |
| 5,827,531 A | 10/1998 | Morrison et al. | |
| 5,830,506 A | 11/1998 | Taylor | |
| 5,874,098 A | 2/1999 | Stevens et al. | |
| 6,103,256 A | 8/2000 | Nabahi | |
| 6,143,716 A | 11/2000 | Meers et al. | |
| 6,238,284 B1 | 5/2001 | Dittgen et al. | |
| 6,251,418 B1 | 6/2001 | Ahern et al. | |
| 6,339,069 B1 | 1/2002 | Meers et al. | |
| 6,367,929 B1 | 4/2002 | Maiden et al. | |
| 6,372,248 B1 | 4/2002 | Qin et al. | |
| 6,372,813 B1 | 4/2002 | Johnson et al. | |
| 2001/0056068 A1* | 12/2001 | Chwalisz et al. ............. 514/21 |
| 2003/0027751 A1* | 2/2003 | Kovesdi et al. ............... 514/12 |

OTHER PUBLICATIONS

Parker et al., *Am. J. Physiol. Lung Cell. Mol.*, 2000;278:L374-L381.*
Xiao et al., *Hypertension*, 2001;37 [part 2]:645-650.*
Meyrick, B. et al., *Am. J. Physiology* 239(5): H692 (1980).
Tanino, Y., *Nippon Rinsho* 59(6): 1076 (2001).

* cited by examiner

*Primary Examiner*—San-Ming Hui
(74) *Attorney, Agent, or Firm*—The McCallum Law Firm, P.C.

(57) ABSTRACT

Methods are provided for the treatment of pulmonary hypertension and other conditions associated therewith. In particular, the methods include treatment of pulmonary hypertension with estradiol metabolite or estradiol metabolite associated with biodegradable microparticles or nanoparticles alone or in combination with another therapeutic agent. Preferred estradiol metabolites include 2-methoxyestradiol, 4-methoxyestradiol, 2-hydroxyestradiol, and 4-hydroxyestradiol, and/or to synthetic derivatives and analogues thereof or prodrugs thereof. The compositions may also be in the form of a controlled release formulation.

27 Claims, 9 Drawing Sheets

Figure 9

ESTRADIOL METABOLITES FOR THE TREATMENT OF PULMONARY HYPERTENSION

RELATED APPLICATIONS

This application claims priority from U.S. Provisional Application No. 60/448,118 filed Feb. 20, 2003.

FIELD OF THE INVENTION

The present invention relates to methods of treating pulmonary hypertension and its sequelae including heart failure and pulmonary and cardiac dysfunction using estradiol metabolites. More particularly, the present invention relates to the use of estradiol metabolites with little estrogenic activity such as 2-hydroxyestradiol, 4-hydroxyestradiol, 2-methoxyestrodiol, and 4-methoxyestradiol, all of which may be delivered in a controlled release formulation for the treatment of pulmonary hypertension and associated conditions.

BACKGROUND OF THE INVENTION

Pulmonary hypertension (PH) is a complex health problem characterized by elevated blood pressure in the lungs. In an individual with PH, the blood pressure in the pulmonary arteries rises far above the normal level of approximately 14 mm Hg at rest. Typical levels found in a PH patient range from 25 mm Hg at rest up to 30 mm Hg or greater during exertion. This elevated pressure is associated with changes in the small blood vessels in the lungs, resulting in an increased resistance to blood flow through those vessels. This increased resistance, in turn, places a strain on the right ventricle of the heart, which then has to work harder than usual to move an adequate amount of blood through the lungs.

Over time, scarring or fibrosis of the blood vessels in the lungs makes such vessels more resistant to blood flow and some may become completely blocked. Additionally, the presence of scarring within the vessels and inflammation in the lungs increases their overall weight. The continual increase in scar tissue and the extra resistance in the blood vessels results in the heart having to pump much harder in order to move blood through the compromised vessels. Eventually, the heart will enlarge in order to meet that demand and the increase in size is associated with reduced contractility and efficiency which can ultimately lead to heart failure. Unfortunately, it is not until this point that most individuals suffering from PH are diagnosed and treatment started.

There is no cure for PH. Several treatment options exist and include therapeutics to increase blood flow such as anticoagulants to prevent blood clots from forming and calcium channel blockers to relieve constriction in the pulmonary arteries. Additionally, constricted vessels may be relieved by the continuous intravenous or subcutaneous infusion of prostacyclin or prostacyclin analogues through an indwelling catheter. Other therapies include the administration of endothelin antagonists to reduce pulmonary arterial pressure, diuretics to reduce systemic fluid accumulation, digoxin to increase the efficiency of cardiac output, and supplemental oxygen to increase the supply of oxygen to the blood. A PH patient may be on one or a combination of treatments at any given time.

Unfortunately, many patients respond poorly to these therapies or stop responding to them over time. The only remaining option at that point in time is a lung transplant. According to the United Network for Organ Sharing (UNOS) the patient survival rates for all patients that had a lung transplant are 85% at one month, 69% at one year, and 51% at three years for patients transplanted between 1987 and 1992. Results since those years are slightly better. An additional obstacle for patients with PH can be the need for both a heart and lung transplant due to heart failure. An effective therapeutic is needed to help patients of all ages and of either gender as an alternative to this risky and very expensive last resort.

The present invention is particularly useful because the estradiol metabolites used therein have few side effects. In addition, estradiol metabolites can be administered in pharmaceutical formulations that provides for sustained release, an improvement that will provide for the widespread use of the compositions as therapeutics for the treatment of pulmonary hypertension and associated conditions.

Citation of the documents herein is not intended as an admission that any is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

Methods are provided for treating pulmonary hypertension and other conditions associated therewith in an individual, including heart failure.

These and other objects of the invention are achieved by one or more of the following embodiments.

In one aspect, the invention features a method for treating pulmonary hypertension in an individual, comprising: administering to the individual a therapeutically effective amount of a composition comprising an estradiol metabolite.

In a preferred embodiment, the estradiol metabolite is selected from the group consisting of 2-hydroxyestradiol, 2-methoxyestradiol, 4-hydroxyestradiol and 4-methoxyestradiol.

In another preferred embodiment, the composition is a prodrug of the estradiol metabolite.

In a further preferred embodiment, the composition comprises a controlled release formulation.

In another aspect, the invention features a method for treating pulmonary hypertension to lower central venous pressure in an individual, comprising: administering to the individual a therapeutically effective amount of a composition comprising an estradiol metabolite.

In a further aspect, the invention features a method for treating pulmonary hypertension to decrease the heart weight of the individual, comprising: administering to the individual a therapeutically effective amount of a composition comprising an estradiol metabolite.

In yet another aspect, the invention features a method for treating pulmonary hypertension to decrease the lung weight of the individual, comprising: administering to the individual a therapeutically effective amount of a composition comprising an estradiol metabolite.

In another aspect, the invention features a method for treating pulmonary hypertension to decrease right ventricular hypertrophy in an individual, comprising: administering to the individual a therapeutically effective amount of a composition comprising an estradiol metabolite.

In a further aspect, the invention features a method for treating pulmonary hypertension to decrease pulmonary vascular resistance in an individual, comprising: administering to the individual a therapeutically effective amount of a composition comprising an estradiol metabolite.

In another aspect, the invention features a method for treating pulmonary hypertension to decrease pulmonary vascular fibrosis in an individual, comprising: administering to the individual a therapeutically effective amount of a composition comprising an estradiol metabolite.

In yet another aspect, the invention features a method for treating pulmonary hypertension to reduce inflammation, cellular proliferation, vascular remodeling and vascular endothelial growth factor expression in the lungs, heart and pulmonary arteries in an individual, comprising: administering to the individual a therapeutically effective amount of a composition comprising an estradiol metabolite.

In a further aspect, the invention features a method for treating heart failure in an individual, comprising: administering to the individual a therapeutically effective amount of a composition comprising an estradiol metabolite.

Other features and advantages of the invention will be apparent from the following description of the preferred embodiment, and from the claims.

BRIEF DESCRIPTION OF THE DRAWINGS

The following figures form part of the present specification and are included to further demonstrate certain embodiments. These embodiments may be better understood by reference to one or more of these drawings in combination with the detailed description of specific embodiments presented herein.

FIG. 2 shows the effects of treatments on heart weight (left panel) ("Heart") and the ratio of heart weight to body weight (right panel) ("Heart/B.W.") according to the present invention. Animals were treated with subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME")(10 µg/kg/hour) (n=7). The left Y-axis is in units of grams and right Y-axis is in units of grams per kg body weight. Data were analyzed by a 1-Factor Analysis of Variance (1F-Anova) to obtain overall differences among the means of each group. Post hoc comparisons (asterisks) were done with Fisher's Least Significant Difference test.

DETAILED DESCRIPTION OF THE INVENTION

I. Definitions

The term "biodegradable" refers to polymers that dissolve or degrade in vivo within a period of time that is acceptable in a particular therapeutic situation. This time is typically less than five years and usually less than one year after exposure to a physiological pH and temperature, such as a pH ranging from 6 to 9 and a temperature ranging from 25° C. to 40° C.

"Pulmonary Hypertension" or "PH" refers to any one or all of the symptoms associated with pulmonary hypertension. The diagnostic categories of PH include, but are not limited to, Pulmonary Arterial Hypertension, Primary Pulmonary Hypertension, Pulmonary Arterial Hypertension Related to Other Causes, Pulmonary Hypertension Associated with Disorders of the Respiratory System, Pulmonary Hypertension due to Chronic Thrombotic or Embolic Disease, Pulmonary Hypertension Due to Disorders Directly Affecting the Pulmonary Blood Vessels, Pulmonary Arterial Hypertension related to collagen vascular diseases, Pulmonary Hypertension associated with chronic HIV infection, Pulmonary Hypertension associated with Drugs or Toxins, and Pulmonary Venous Hypertension. Additionally, a PH patient may be at risk or currently suffering from heart failure due to the increase in central venous pressure. Due to the many manifestations of the disease called PH, the present invention will use the term "Pulmonary Hypertension" or "PH" to refer to any or all of the above disorders.

The term "estradiol" refers to 17β-estradiol.

The term "estradiol metabolite(s)" refers to metabolites of 17β-estradiol such as catecholestradiols and methoxyestradiols which exert little estrogenic activity and have a low affinity for the estrogen receptor and/or to synthetic derivatives and analogues thereof, examples of which include but are not limited to 2-methoxyestradiol, 4-methoxyestradiol, 2-hydroxyestradiol and 4-hydroxyestradiol.

"Individual" refers to an animal or human of either gender.

The term "prodrug" refers to a compound that releases an estradiol metabolite.

According to the present invention, an isolated or biologically pure estradiol metabolite is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

II. Methods

The present invention provides methods of using estradiol metabolites to treat PH and associated conditions such as heart failure and pulmonary and cardiac dysfunction. Specifically, the present invention provides methods for lowering central venous and/or arterial pressure in an individual with PH as well as decreasing the heart weight, lung weight, right ventricular hypertrophy, vascular resistance, vascular fibrosis and reducing inflammation, cellular proliferation, vascular remodeling and vascular endothelial growth factor (VEGF) expression in the lungs, heart and pulmonary arteries in such an individual. The invention also provides methods of administering a therapeutically effective amount of a composition containing an estradiol metabolite for the treatment of such disorders.

Estradiol metabolites used to carry out the methods of the present invention include metabolites of 17β-estradiol such as catecholestradiols and methoxyestradiols which exert little estrogenic activity and have low affinity for the estrogen receptor, examples of which include 2-methoxyestradiol, 4-methoxyestradiol, 2-hydroxyestradiol and 4-hydroxyestradiol as well as others including synthetic derivatives and analogues thereof. Such estradiol metabolites may be incorporated in a controlled release formulation and also may be combined with another therapeutic agent. Such estradiol metabolites may also be released from prodrugs.

Biodegradable microparticles or nanoparticles that may be used in a controlled release formulation include one or more polymers such as poly(lactide)s, poly(glycolide)s, poly (lactide-co-glycolide)s, poly(lactic acid)s, poly(glycolic acid)s, poly(lactic acid-co-glycolic acid)s, polycaprolactone, polycarbonates, polyesteramides, polyanhydrides, poly (amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, and blends and copolymers thereof.

Estradiol Metabolites

Estradiol metabolites used in accordance with the present invention include catecholestradiols such as 2-hydroxyestradiol (estra-1,3,5 (10)-triene-2,3,17-triol (17β)) or 4-hydroxyestradiol (estra-1,3,5 (10)-triene-3,4,17-triol (17β)) or methoxyestradiols, such as 2-methoxyestradiol (estra-1,3,5 (10)-triene-2-methoxy-3, 17-diol (17β)) or 4-methoxyestradiol (estra-1,3,5 (10)-triene-4-methoxy-3,17-diol (17β)). Commercial preparations of all of these compounds are readily available.

Estradiol metabolites may also be incorporated into a controlled release formulation. Such controlled release formulations may be biodegradable microparticles, biodegradable nanoparticles, patches, crystals, gels, hydrogels, liposomes, and the like. In addition, the estradiol metabolites may be incorporated into devices such as implants, vaginal rings, osmotic pumps, diffusion devices and transdermal delivery devices. According to the present invention prodrugs of estradiol metabolites and/or synthetic derivatives and analogues thereof may also be used. Specific examples include esters of hydroxyestradiols and methoxyestradiols.

It will be apparent to the skilled artisan that the compounds listed above are exemplary only and that many variations may be used, depending on the particular hydroxylation or methylation site on the parent estradiol compound. For example, estradiol can be hydroxylated or methylated at many sites and such variations are known in the art.

Modes of Administration

Therapeutic compositions of the present invention can be formulated in an excipient that the individual to be treated can tolerate. Examples of such excipients include water, saline, Ringer's solution, dextrose solution, Hank's solution, and other physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability.

Examples of buffers that may be used to practice the present invention include phosphate buffer, bicarbonate buffer and Tris buffer, while examples of preservatives include thimerosal, cresols, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline is added prior to administration.

The present invention also can be practiced using suitable topical, oral, systemic and parenteral formulations of the pharmaceutical compounds herein provided. The formulations can be administered in a wide variety of therapeutic dosage forms in conventional vehicles for administration. For example, the compounds can be formulated for oral administration in the form of tablets, capsules (each including timed release and sustained release formulations), pills, powders, granules, elixirs, tinctures, solutions, suspensions, syrups and emulsions. Likewise, they may also be administered intravenously (both bolus and infusion), during angioplasty/catheterization, intraperitoneally, subcutaneously, topically with or without occlusion, or intramuscularly, all using forms well known to those of ordinary skill in the pharmaceutical arts.

Therapeutic compositions of the present invention can also include a carrier. Carriers include compounds that increase the half-life of a therapeutic composition in the treated individual. Suitable carriers include, but are not limited to, polymeric controlled release vehicles, biodegradable implants, liposomes, bacteria, viruses, other cells and glycols.

Controlled Release Formulations

The methods of the present invention can also employ controlled release formulations that are capable of slowly releasing a composition of the present invention into an individual. As used herein, a controlled release formulation can include a composition of the present invention in a controlled release vehicle. Such controlled release formulations are well known in the art. Suitable controlled release formulations include, but are not limited to, biocompatible polymers, other polymeric matrices, capsules, microcapsules, microparticles, nanoparticles, patches (See, U.S. Pat. Nos. 6,238,284 and 5,736,154), crystals (See U.S. Pat. No. 5,827,531), bolus preparations, liposomes (See, U.S. Pat. Nos. 6,339,069 and 6,143,716) liospheres, gels (See, U.S. Pat. No. 5,830,506) and hydrogels (See, U.S. Pat. Nos. 6,372,813; 6,372,248; and 6,367,929). Such controlled release vehicles also include devices, such as vaginal rings (See, U.S. Pat. Nos. 6,103,256 and 5,788,980), implants (See, U.S. Pat. Nos. 6,251,418 and 5,874,098), osmotic pumps, diffusion devices, and transdermal delivery systems. Other controlled release formulations of the present invention include liquids and suspensions that, upon administration to an individual, form a solid or a gel in situ. Preferred controlled release formulations are biodegradable. All such compositions are well known in the art.

The methods of the present invention can also employ controlled release formulations that are capable of releasing a composition of the present invention into an individual at a rate sufficient to attain and maintain therapeutic dose levels of the composition. A therapeutic composition is preferably released over a period of time ranging from 1 day to about 12 months. More preferably, such therapeutic composition is released over a 2 to 30 day time period.

Dosage

Parameters in the dosage regime may be varied to administer therapeutic compositions of the present invention in an effective manner. Such parameters include individual dose size, number of doses, frequency of dose administration, and mode of administration. Variation of such parameters can be accomplished by those skilled in the art. A suitable single dose is a dose that is capable of protecting (i.e. preventing or treating) an animal or human from disease when administered one or more times over a suitable time period. The need for additional administrations of a therapeutic composition can be determined by one of skill in the art in accordance with the given condition of a patient.

Treatment of Pulmonary Hypertension

Pulmonary Hypertension is divided into five primary categories. The first is Pulmonary Arterial Hypertension (PAH) and includes patients with pulmonary arterial damage. There are two types of PAH, Primary Pulmonary Hypertension (PPH) and Pulmonary Arterial Hypertension Related to Other Causes. Primary Pulmonary Hypertension occurs without any apparent cause, although approximately 10% of cases appear to have a genetic component since it occurs in families with a history of PPH. Additionally, term or post-term infants may demonstrate difficulty with cardiac or pulmonary function. This type of PPH is called Persistent Pulmonary Hypertension of the Newborn and is characterized by cyanosis and respiratory distress with tachypnea. Radiographs of an infant's chest may demonstrate various abnormalities compatible with aspiration, pneumonia, diaphragmatic hernia or hyaline membrane disease. A diagnosis of Persistent Pulmonary Hypertension of the Newborn can be confirmed echocardiographically.

Pulmonary Arterial Hypertension Related to Other Causes is associated with exposure to toxins such as diet drugs containing fenfluramine or dexfenfluramine, illegal substances like cocaine or methamphetamine or contaminated food or water. Other causes of this subcategory of PAH include diseases, such as the Human Immunodeficiency Virus (HIV) infection; collagen vascular diseases, such as scleroderma, lupus, or rheumatoid arthritis; or liver diseases, such as chronic liver disease or portal vein obstruction.

A second category of PH is Pulmonary Hypertension Associated with Disorders of the Respiratory System. This is often seen in patients already suffering from emphysema, asthmatic bronchitis, sleep apnea, chronic obstructive pulmonary disease, interstitial lung disease, sleep disordered breathing, alveolar hypoventilation disorder, neonatal lung disease, alveolar-capillary dysplasia or chronic exposure to high altitude.

A third category of Pulmonary Hypertension is due to Chronic Thrombotic or Embolic Disease. This is often seen in patients that have presented with blood clots in their pulmonary arteries, a pulmonary embolism or sickle cell disease. Additionally patients with obstruction of distal pulmonary arteries, such as by thrombus, a tumor, parasites or foreign material, are also classified as having PH due to Chronic Thrombotic or Embolic Disease.

A fourth category of Pulmonary Hypertension is due to Disorders Directly Affecting the Pulmonary Blood Vessels. This category is often observed in patients with inflammatory diseases, such as schistosomiasis or sarcoidosis or pulmonary capillary disease.

A fifth category is Pulmonary Venous Hypertension (PVH). This is caused by diseases or defects of the left side of the heart, such as left-sided atrial or ventricular heart disease; left-sided valvular heart disease; extrinsic compression of central pulmonary veins, such as with fibrosing mediastinitis or adenopathy or tumors; or pulmonary veno-occlusive disease. Patients suffering from PVH demonstrate an increase pulmonary artery pressure but this rarely leads to severe PAH.

The early symptoms of PH include shortness of breath, a continual feeling of being tired, dizziness, fainting, swollen ankles or legs and chest pain. Upon further assessment of a patient's heart and lungs via echocardiogram, electrocardiogram, right heart catheterization, a six-minute walk test and/or an assessment of function in tasks of daily living, they may not fit into a particular diagnostic category but have many of the criteria for PH. Additionally, patients with PH of any type are at risk of heart failure due to the continual increase in central venous pressure. Due to the many manifestations of the disease called PH, the present invention will use the term "Pulmonary Hypertension" or "PH" to refer to any subset of the above-listed symptoms.

In treating PH according to the present invention, estradiol metabolites may be incorporated into biodegradable microparticles or nanoparticles and may be administered to the patient. It is also within the scope of the present invention to administer estradiol metabolites which have been associated with biodegradable microparticles or nanoparticles with at least one other agent for the treatment of PH ("PH agent"). A PH agent may be, for example, an anticoagulant, calcium channel blocker, prostacyclin, prostacyclin analogue, diuretic, digoxin, endothelin antagonist, phosphodiesterase inhibitor, prostaglandin analogue, nitric oxide, adenosine, oxygen, or any other suitable agent. Treatment may be achieved by administering a single composition or pharmacological formulation that includes both an estradiol metabolite and a PH agent or by treating the patient with two distinct compositions or formulations simultaneously, wherein one composition includes the estradiol metabolite, with or without an association with a biodegradable polymer, and the other includes the PH agent Alternatively, any of the estradiol metabolite treatments may precede or follow the PH agent treatment by intervals ranging from minutes to weeks. In instances where the PH agent and any of the estradiol metabolites are administered separately, one would generally ensure that a significant period of time did not expire between the time of each delivery, such that the PH agent and estradiol metabolite would still be able to exert an advantageously combined (e.g., synergistic) effect on the condition. In such instances, it is contemplated that one would administer the two therapeutics within about 12–24 hours of each other, and, more preferably, within about 6–12 hours of each other, with a delay time of only about 12 hours being most preferred. In some situations, it may be desirable to extend the duration of treatment with just the therapeutic agent, for example, where several days (2, 3, 4, 5, 6, or 7) to several weeks (1, 2, 3, 4, 5, 6, 7 or 8) lapse between the respective administrations. Agents suitable for use in combination therapy are any chemical compound or treatment method useful to patients with PH.

In treating pulmonary hypertension according to the present invention, estradiol metabolites which may be incorporated into biodegradable microparticles or nanoparticles, and may also be co-administered with another agent, will work to prevent and/or treat pulmonary vascular hypertrophy and fibrosis. This will function to lower pressure in the pulmonary vasculature and/or lessen both heart and lung pathology.

The present invention will now be further illustrated, but is by no means limited to, the following example. It will be apparent to those skilled in the art that the techniques described in the example represent techniques discovered by the inventors to function well in the practice of the invention, and thus can be considered to constitute presently preferred modes for its practice. However, it should be apparent to those of skill in the art that many modifications, both to materials and methods may be made in the specific embodiments without departing from the spirit and scope of this invention.

EXAMPLE 1

Experimental Design:

A total of twenty-seven, male Sprague Dawley rats (Charles River, Wilmington, Mass.) (378 +/−12 grams) were utilized in this experiment. Animals were housed in the University of Pittsburgh Medical Center animal care facility (temperature 22° C., light cycle 12 hours, relative humidity 55%). Animals were fed Pro Lab RHM 3000 rodent diet (PMI Nutrition, Inc, St Louis, Mo.) and were given water ad libitum. Institutional guidelines for animal welfare were followed, and the Animal Care and Use Committee approved experimental protocols.

Animals were randomly assigned to receive subcutaneously saline (1 ml/kg, n=6) or monocrotaline (Sigma, St Louis, Mo.) (MCT, 60 mg/kg subcutaneously) (n=21). Monocrotaline is an agent known to induce pulmonary hypertension. Six hours after the initial injection, control animals were implanted with osmotic minipumps (model 2ML4, Alza, Palo Alto, Calif.) containing vehicle (polyethylene glycol 400, 2.5 µl/hour) (Sigma, St Louis, Mo.), whereas MCT treated animals were implanted with osmotic minipumps containing either vehicle (MCT group; n=7), 2-hydroxyestradiol (Steraloids, Newport, R.I.) (10 μg/kg/hour, MCT+2HE group, n=7) or 2-methoxyestradiol (Steraloids, Newport, R.I.) (10 μg/kg/hour, MCT+2ME group, n=7). Assignment to the MCT, MCT+2HE, and MCT+2ME groups was conducted randomly.

After 21 days animals were weighed, anesthetized with pentobarbital (Sigma, St Louis, Mo.) (50 mg/kg) intraperitoneally, and instrumented for measurements of blood pressure, heart rate and central venous pressure. A PE-50 catheter was inserted into the right jugular vein and advanced approximately one inch and connected to a low-pressure analyzer (LPA, Micro-Med., Inc., Louisville Ky.) for continuous measurements of central venous pressure. Another PE-50 catheter was inserted into left carotid artery and connected to a blood-pressure analyzer (BPA, Micro-Med., Inc., Louisville Ky.) for continuous measurement of blood pressure and heart rate. A 22-G needle connected to a PE-50 catheter was inserted into the tail vein for delivery of supplemental anesthetics. After 60 minutes, a 30-minute recording of hemodynamic parameters was conducted.

Animals were killed by an overdose of anesthetic, and the heart and lungs were removed and weighed. Both atriums were carefully removed, and the right ventricle was carefully dissected from the left ventricle. Both ventricles were weighed and the right ventricle to left ventricle plus septum ratio was calculated.

The right ventricle, left ventricle, main pulmonary artery and the right inferior lobes of the lungs were cut and fixed with 10% formalin buffer. The fixed specimens were embedded in paraffin and cut into 4-micron-thick sections for subsequent light microscopy and immunohistochemical analysis.

For the assessment of proliferation, the proliferating cell nuclear antigen (PCNA) was labeled using the primary monoclonal mouse antibody (1/200 dilution; Dako, Carpenteria, Calif.) and VEGF expression was measured using a rabbit polyclonal antibody (1/50 dilution, Lab Vision, Fremont, Calif.). A polyclonal ED1 antibody (Serotec, Raleigh, N.C.) specific for the monocyte/macrophage cytoplasmatic antigen was used to label vascular (main pulmonary artery) and pulmonary macrophages. For measurement of nonspecific staining, the primary antibody was replaced with phosphate buffered saline (PBS). Sections were washed and further developed according to the directions of the manufacturer (Dako Corporation, Carpinteria, Calif.) using the LSAB2 kit that contained a second antibody linked to avidin and peroxidase conjugated biotin. Immunochemical staining for PCNA and VEGF were assessed quantitatively with a SAMBA 4000 image analyzer (Image Products International, Chantilly, Va.) using specialized computer software designed for immunostaining analysis (Immuno-Analysis, version 4.1, Microsoft, Richmond, Wash.). The software set density threshold values by averaging several fields on the negative control tissues in which the primary antibody was replaced with PBS. Background subtraction was then performed on every tissue. Ten high power fields (×400) were assessed for staining density, wall thickness or positively marked cells for ED-1. The results for PCNA and VEGF are reported as the labeling index, which represents the percentage of the total examined area that stained positively. Staining intensity of positive areas was also assessed (mean optical density), and a mean quick score was then calculated (mean optical density×labeling index). The inflammatory response data are expressed as the total number of ED1+ cells per ten high power fields For assessment of vascular remodeling, vascular smooth muscle cells in pulmonary arteries were stained with smooth muscle alpha-actin Ab-1 mouse monoclonal antibody (1/100 dilution, Lab Vision, Fremont, Calif.). The wall and media thickness were measured in small size pulmonary arteries (50–200 microns) using commercial imaging software. Only vessels with an approximately circular profile were analyzed.

Statistical analyses were performed using the Number Cruncher Statistical software program (Kaysville, Utah). Group comparisons were performed by a one-factor analysis of variance (1-F ANOVA), followed by post-hoc comparison using the Fisher's LSD test. All data are presented as mean ±S.E.M.

Results:

Administration of monocrotaline to laboratory animals is used to create a model of pulmonary hypertension (See, e.g., B. Meyrick et al., *Am. J. Physiology* 239(5): H692 (1980), and Tanino, Y., *Nippon Rinsho* 59(6): 1076 (2001), the disclosures of which and incorporated herein by reference.) Initially, structural changes in the small and large pulmonary arteries occur as the monocrotaline induces proliferation of the myointima in the vessels. This leads to an increase in pulmonary alveolar macrophage activity which results in an increased lung weight and, in turn, stimulates various inflammatory mediators. All of these changes in the lungs due to the administration of monocrotaline result in an increase in pulmonary vascular resistance and right ventricular hypertrophy which results in an increase in the weight of the right ventricle.

Figure 1:
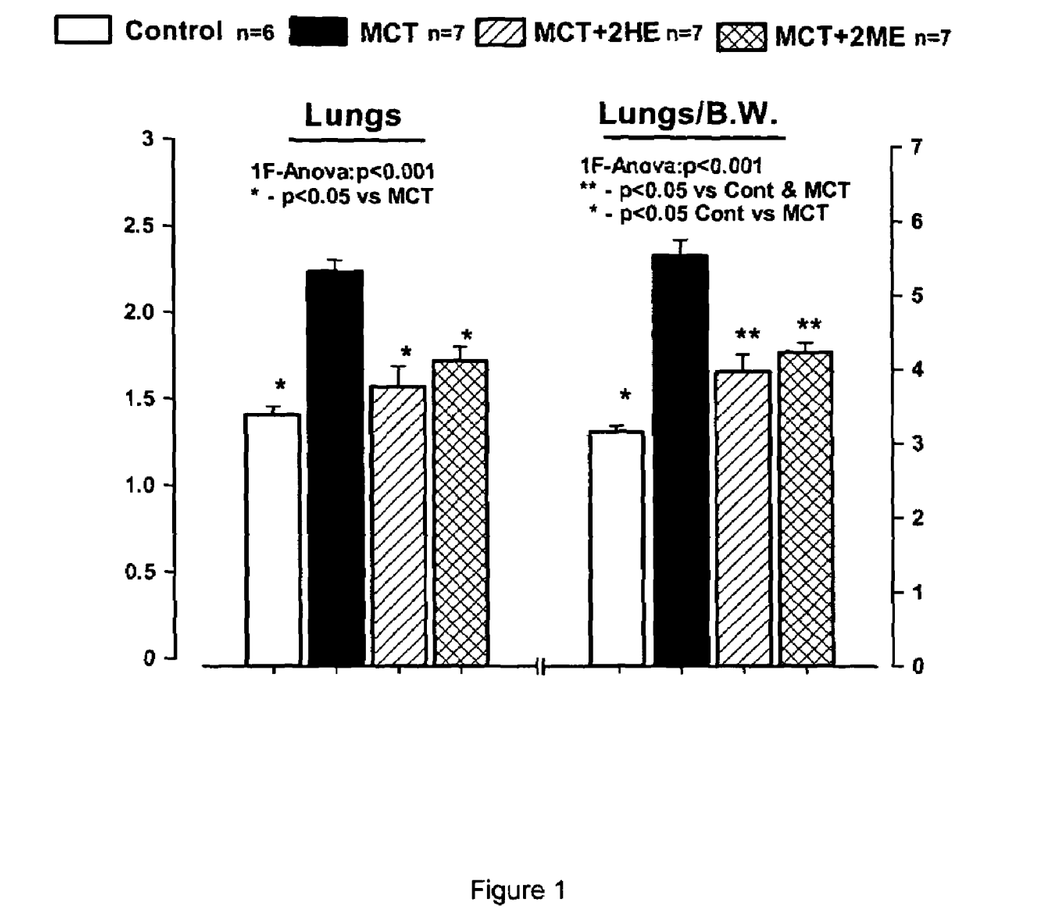
FIG. 1 shows the effects of subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME") (10 µg/kg/hour) (n=7) on lung weight (left panel) ("Lungs") and the ratio of lung weight to body weight (right panel) ("Lungs/B.W.") according to the present invention. The left Y-axis is in units of grams and right Y-axis is in units of grams per kg body weight. Data were analyzed by a 1-Factor Analysis of Variance (1F-Anova) to obtain overall differences among the means of each group. Post hoc comparisons (asterisks) were done with Fisher's Least Significant Difference test.
Figure 2:
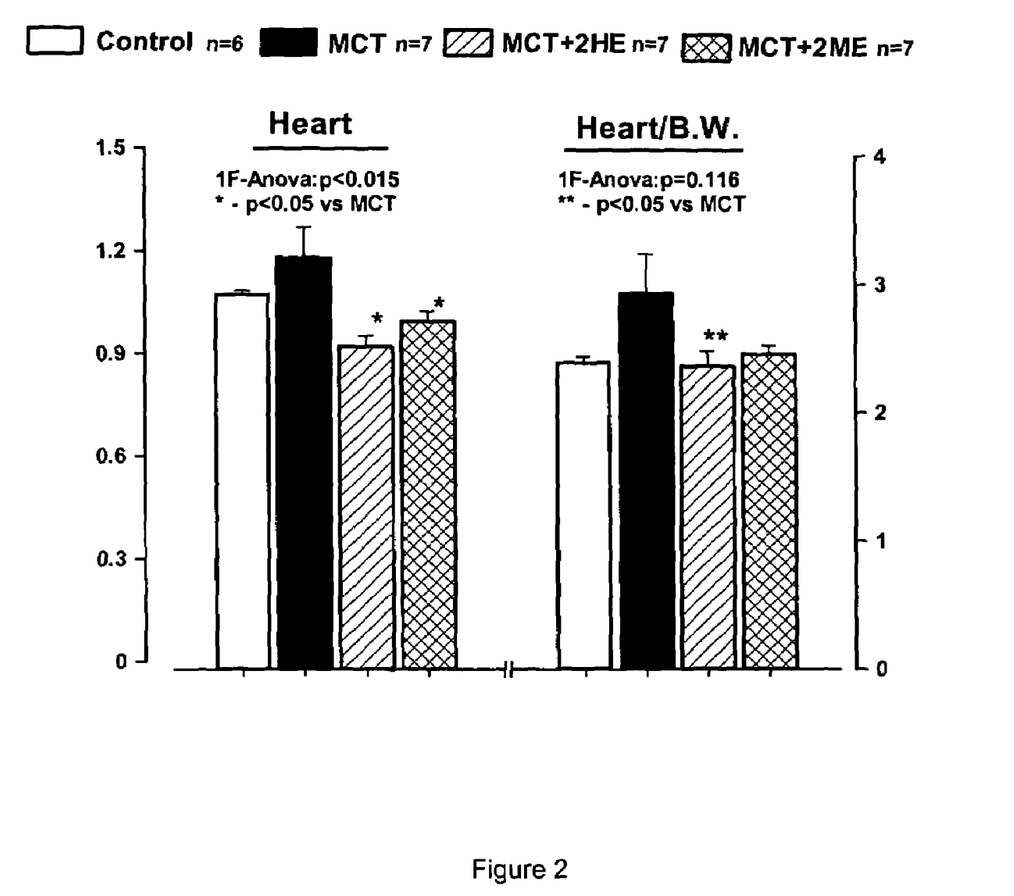
Figure 3:
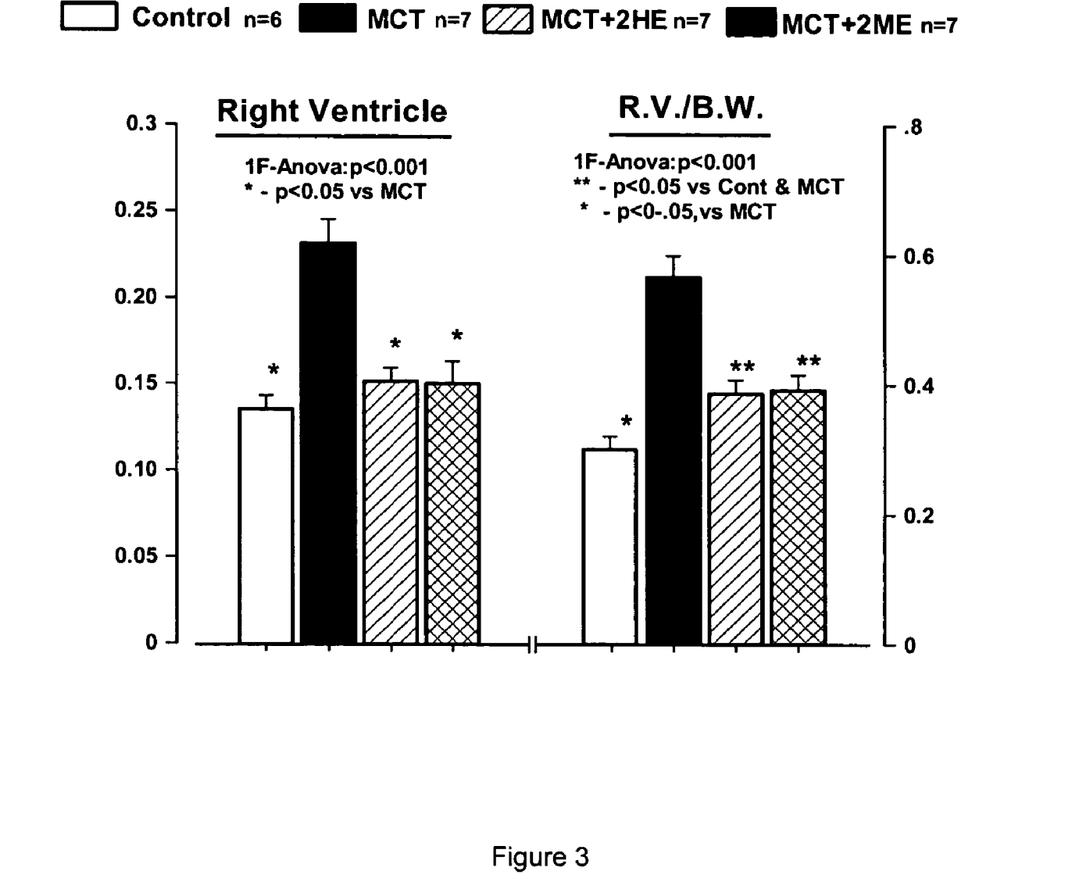
FIG. 3 shows the effects of subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME")(10 µg/kg/hour) (n=7) on right ventricular weight (left panel) ("Right Ventricle") and the ratio of right ventricular weight to body weight (right panel) ("R.V./B.W.") according to the present invention. The left Y-axis is in units of grams and the right Y-axis is in units of grams per kilogram body weight. Data were analyzed by a 1-Factor Analysis of Variance (1F-Anova) to obtain overall differences among the means of each group. Post hoc comparisons (asterisks) were done with Fisher's Least Significant Difference test
Figure 4:
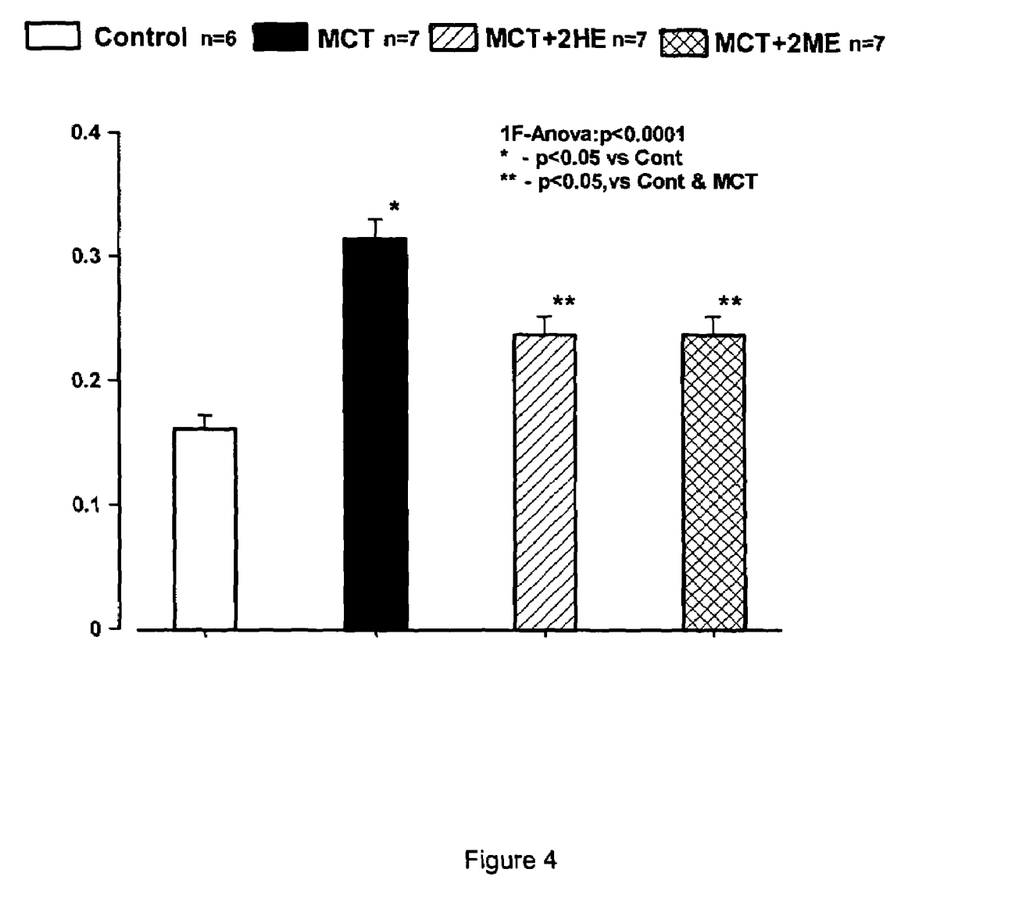
FIG. 4 shows the effects of subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME") (10 µg/kg/hour) (n=7) on the ratio derived by dividing the weight of the right ventricle by the weight of the left ventricle plus septum. Data were analyzed by a 1-Factor Analysis of Variance (1F-Anova) to obtain overall differences among the means of each group. Post hoc comparisons (asterisks) were done with Fisher's Least Significant Difference test.
Figure 5:
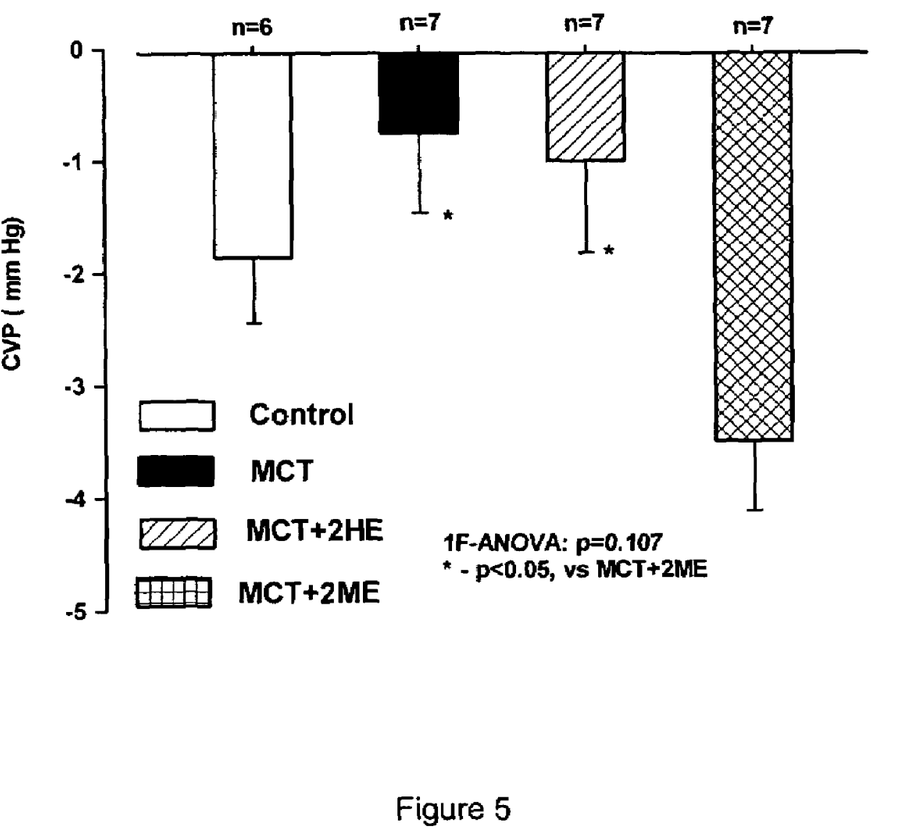
FIG. 5 shows the effects of subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME") (10 µg/kg/hour) (n=7) on central venous pressure ("CVP") according to the present invention. Data were analyzed by a 1-Factor Analysis of Variance (1F-Anova) to obtain overall differences among the means of each group. Post hoc comparisons (asterisks) were done with Fisher's Least Significant Difference test.

Administration of monocrotaline in this experiment caused the expected results. There was an observable increase in lung weight, as seen in FIG. 1, and a marked increase in pulmonary vascular resistance in these animals. The increase in pulmonary vascular resistance resulted in pulmonary hypertension which, in turn, caused cardiac hypertrophy as seen in FIG. 2, and right ventricular hypertrophy and an increase in right ventricular weight, as seen in FIG. 3, in animals treated with monocrotaline. Additionally, monocrotaline-treated animals demonstrated a greater ratio of the weight of the right ventricle to the left ventricle plus the septum, as seen in FIG. 4. Central venous pressure, a hallmark of pulmonary hypertension and heart failure, was also higher in monocrotaline-treated animals as shown in FIG. 5.

In contrast, animals treated with monocrotaline and 2-hydroxyestradiol or 2-methoxyestradiol did not demonstrate the same level of adverse consequences associated with monocrotaline treatment. The estradiol metabolites significantly reduced the negative effects of the monocrotaline as these animals did not experience pulmonary hypertension, increased lung weight, cardiac hypertrophy or right ventricular hypertrophy as seen in FIGS. 1, 2, 3, and 4. Additionally, 2-methoxyestradiol was especially effective at reducing central venous pressure which, in turn, protected these animals against heart failure (See FIG. 5).

Figure 6A:
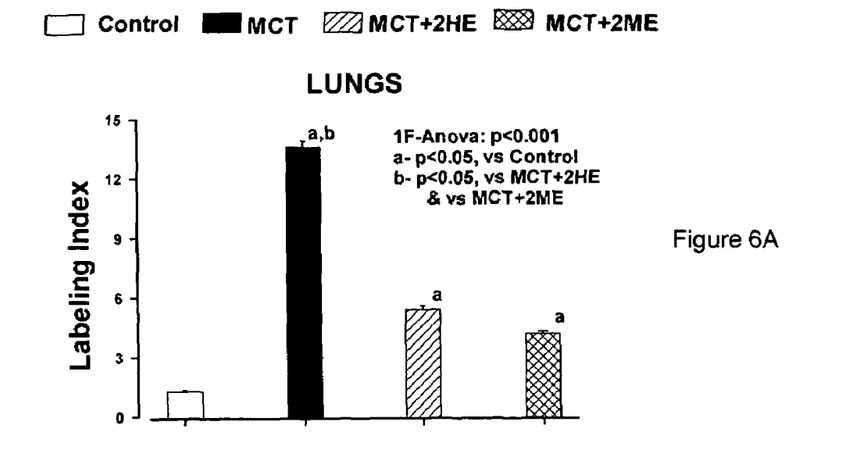
FIGS. 6A–6C show the effects of subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME") (10 µg/kg/hour) (n=7) on cell proliferation (PCNA staining) in lungs (FIG. 6A), right ventricle (FIG. 6B) and pulmonary artery (FIG. 6C). The labeling represents the percentage of the total examined area that stained positively ("Labeling Index"). Data were analyzed by a 1-Factor Analysis of Variance (1F-Anova) to obtain overall differences among the means of each group. Post hoc comparisons (letters) were done with Fisher's Least Significant Difference test.
Figure 6B:
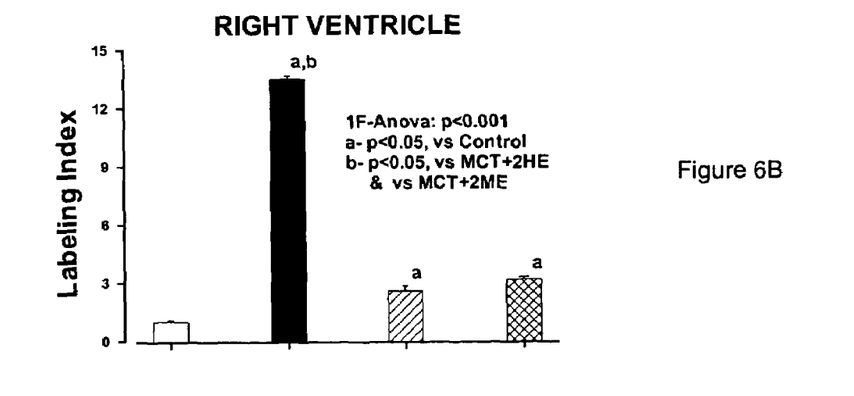
Figure 6C:
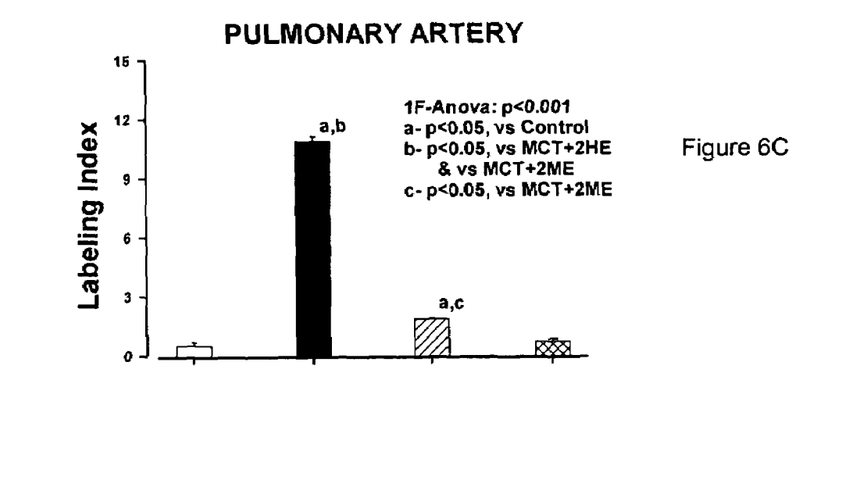

Quantitative analysis of proliferation (PCNA staining) in lungs, right ventricle and the main pulmonary artery are presented in FIGS. 6A–6C, respectively. Monocrotaline-induced endothelial damage and subsequent pulmonary hypertension were accompanied by marked proliferative responses. Increased staining for proliferating cells was detected in the lungs (FIG. 6A), right ventricle (FIG. 6B), and main pulmonary artery (FIG. 6C) in monocrotaline-treated animals as compared with control animals. Distribution of PCNA positive cells in the right ventricle suggested increased proliferation of cardiac fibroblasts; whereas in the pulmonary artery, a pronounced proliferative response was detected in the media and adventitia. Both 2HE and 2ME markedly (p<0.001) inhibited the proliferative response in the lungs (−60% and −70%) (FIG. 6A), right ventricle (−81% and −77%) (FIG. 6B), and main pulmonary artery (−83% and −94%, 2HE and 2ME, respectively; FIG. 6C).

Figure 7A:
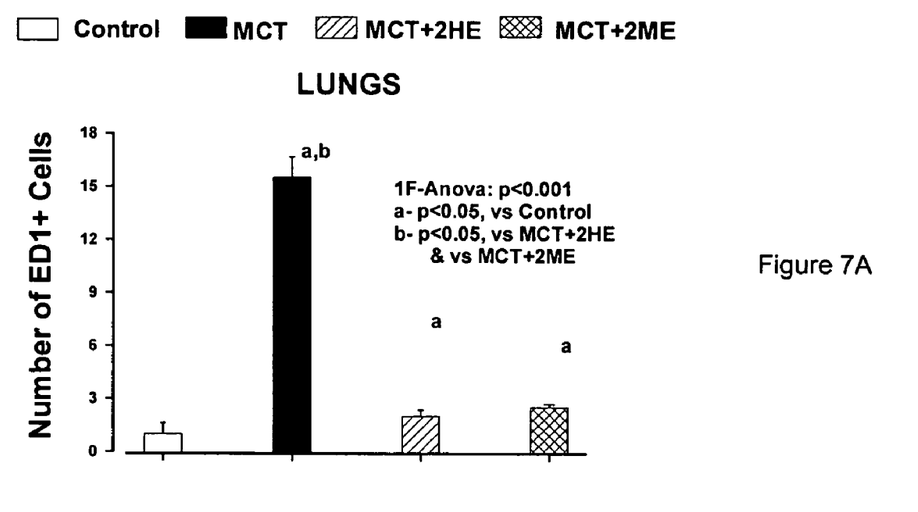
FIGS. 7A and 7B show the effects of subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME") (10 µg/kg/hour) (n=7) on inflammatory cells (ED1+ cells) ("Number of ED1$^+$ cells") in lungs (FIG. 7A) and pulmonary artery (FIG. 7B). Data were analyzed by a 1-Factor Analysis of Variance (1F-Anova) to obtain overall differences among the means of each group. Post hoc comparisons (letters) were done with Fisher's Least Significant Difference test.
Figure 7B:
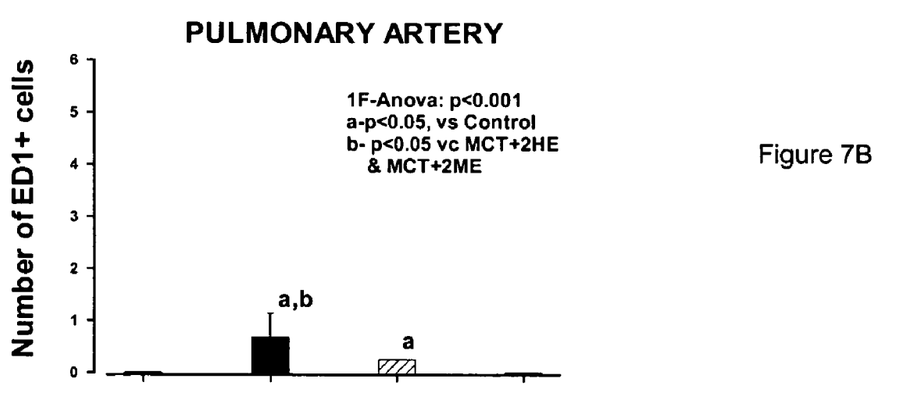
Figure 8:
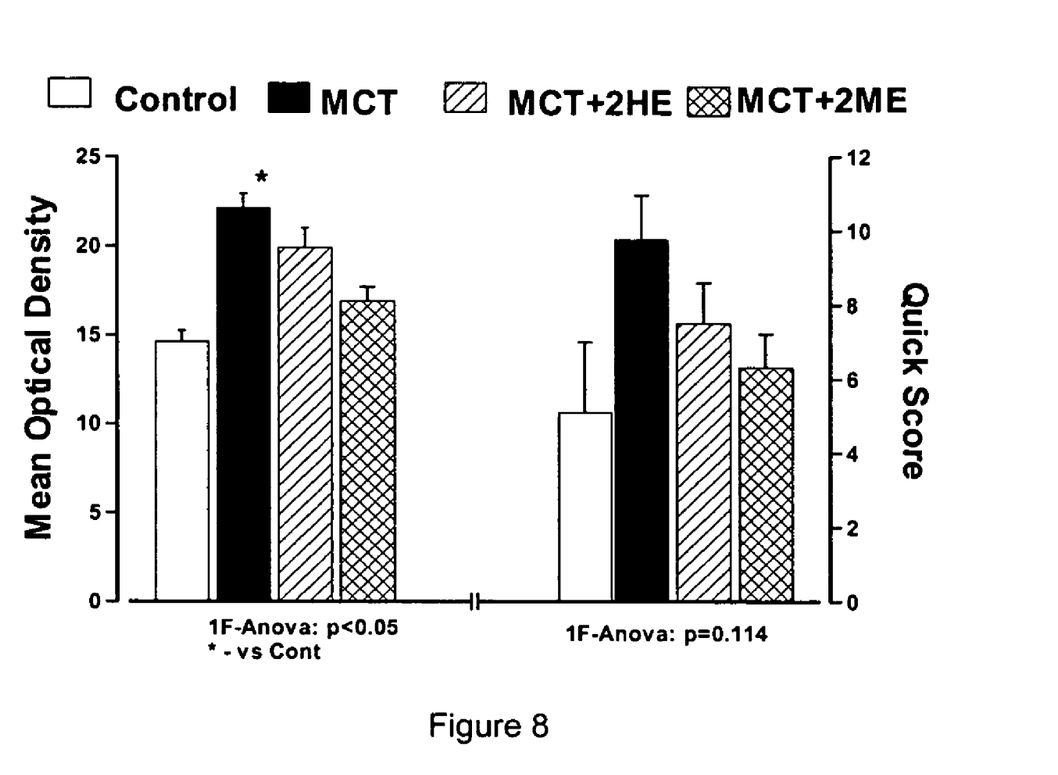
FIG. 8 shows the effects of subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME") (10 µg/kg/hour) (n=7) on vascular endothelial growth factor ("VEGF") expression in the lungs. Staining intensity of positive areas was assessed as the mean optical density (left y-axis) ("Mean Optical Density"); total staining adjusted for mean optical density was assessed as the quick score (right y-axis) ("Quick Score"). Data were analyzed by a 1-Factor Analysis of Variance (1F-Anova) to obtain overall differences among the means of each group. Post hoc comparisons (asterisks) were done with Fisher's Least Significant Difference test.

The development of pulmonary hypertension was also associated with significant inflammation (p<0.001) in the lungs (FIG. 7A, Control vs. MCT, p<0.001). Inflammatory (ED1+) cells were also detected in the pulmonary artery of MCT treated animals (FIG. 7B). Estradiol metabolites almost completely abolished the inflammatory response in the lungs (p<0.001) and inhibited inflammatory cell infiltration in pulmonary artery (FIGS. 7A and 7B, respectively). Immunohistochemical analysis of VEGF expression revealed less notable changes. A similar percent of the lung tissue used stained positive for VEGF (labeling index 34.2±2.2, 42.8±2.6, 37.6±3.3, and 37.6±3.9, Control, MCT, MCT+2HE and MCT+2ME group, respectively; p=0.482). However, the density of the staining (mean optical density) and quick score index were higher in MCT group compared with control animals (FIG. 8).

Figure 9:
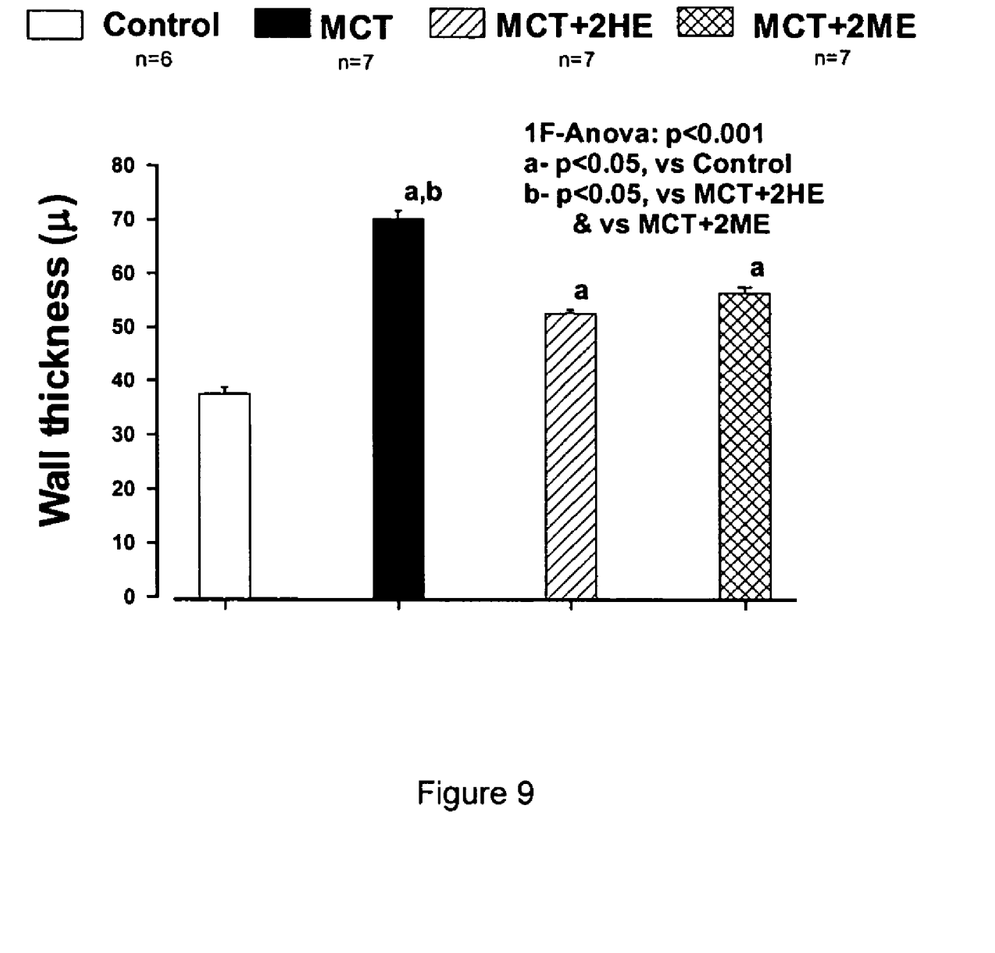
FIG. 9 shows the effects of subcutaneous saline (1 ml/kg) with vehicle (polyethylene glycol 400, 2.5 µl/hour) ("Control") (n=6), subcutaneous monocrotaline ("MCT") (60 mg/kg, n=7) with vehicle (polyethylene glycol 400, 2.5 µl/hour), subcutaneous monocrotaline (60 mg/kg) with 2-hydroxyestradiol ("MCT+2HE") (10 µg/kg/hour) (n=7) and subcutaneous monocrotaline (60 mg/kg) with 2-methoxyestradiol ("MCT+2ME") (10 µg/kg/hour) (n=7) on wall thickness ("Wall Thickness") in microns as assessed by actin staining in small size pulmonary arteries. Data were analyzed by a 1-Factor Analysis of Variance (1F-Anova) to obtain overall differences among the means of each group. Post hoc comparisons (letters) were done with Fisher's Least Significant Difference test.

Semi-quantitative analysis of the VEGF distribution in the lungs of MCT treated rats revealed highest expression in the airways (i.e., epithelium and subepithelial smooth muscle cells). Importantly, both metabolites tended to abolish these changes. The development of pulmonary hypertension in MCT treated animals was associated with marked vascular remodeling. Immunohistochemical analysis of small size pulmonary arteries (smooth muscle alpha-actin staining) detected marked media hypertrophy in MCT rats (increased wall thickness by 87% in MCT groups compared to control animals; FIG. 9). Importantly, both estradiol metabolites attenuated MCT-induced hypertrophy of the media (−50% and −40%, MCT+2HE and MCT+2ME, respectively; p<0.001).

While the disclosed methods and compositions have been described in terms of the specific embodiments of the invention, it will be apparent to those of ordinary skill in the art that variations may be applied without departing from the concept, spirit and scope of the claimed invention. More specifically, it will be apparent that certain agents that are both chemically and physiologically related may be substituted for the agents described herein while the same or similar results would be achieved. All such similar substitutes and modifications apparent to those skilled in the art are deemed to be within the invention as defined by the appended claims. Accordingly, it is understood that the drawings and the descriptions herein are proffered only to facilitate comprehension of the invention and should not be construed to limit the scope hereof.

We claim:

1. A method of treating pulmonary hypertension in an individual, comprising: administering to said individual a therapeutically effective amount of a composition comprising an estradiol metabolite selected from the group consisting of a catecholestradiol and a methoxyestradiol.

2. The method of claim 1, wherein said estradiol metabolite is selected from the group consisting of 2-hydroxyestradiol, 2-methoxyestradiol, 4-hydroxyestradiol and 4-methoxyestradiol.

3. The method of claim 1, wherein said composition comprises a controlled release formulation.

4. A method of treating an individual with pulmonary hypertension to lower central venous pressure in said individual, comprising: administering to said individual a therapeutically effective amount of a composition comprising an estradiol metabolite selected from the group consisting of a catecholestradiol and a methoxyestradiol.

5. The method of claim 4, wherein said estradiol metabolite is selected from the group consisting of 2-hydroxyestradiol, 2-methoxyestradiol, 4-hydroxyestradiol and 4-methoxyestradiol.

6. The method of claim 4, wherein said composition comprises a controlled release formulation.

7. A method of treating an individual with pulmonary hypertension to decrease the heart weight of said individual, comprising: administering to said individual a therapeutically effective amount of a composition comprising an estradiol metabolite selected from the group consisting of a catecholestradiol and a methoxyestradiol.

8. The method of claim 7, wherein said estradiol metabolite is selected from the group consisting of 2-hydroxyestradiol, 2-methoxyestradiol, 4-hydroxyestradiol and 4-methoxyestradiol.

9. The method of claim 7, wherein said composition comprises a controlled release formulation.

10. A method of treating an individual with pulmonary hypertension to decrease the lung weight of said individual, comprising: administering to said individual a therapeutically effective amount of a composition comprising an estradiol metabolite selected from the group consisting of a catecholestradiol and a methoxyestradiol.

11. The method of claim 10, wherein said estradiol metabolite is selected from the group consisting of 2-hydroxyestradiol, 2-methoxyestradiol, 4-hydroxyestradiol and 4-methoxyestradiol.

12. The method of claim 10, wherein said composition comprises a controlled release formulation.

13. A method of treating an individual with pulmonary hypertension to decrease right ventricular hypertrophy in said individual, comprising: administering to said individual a therapeutically effective amount of a composition comprising an estradiol metabolite selected from the group consisting of a catecholestradiol and a methoxyestradiol.

14. The method of claim 13, wherein said estradiol metabolite is selected from the group consisting of 2-hydroxyestradiol, 2-methoxyestradiol, 4-hydroxyestradiol and 4-methoxyestradiol.

15. The method of claim 13, wherein said composition comprises a controlled release formulation.

16. A method of treating an individual with pulmonary hypertension to decrease pulmonary vascular resistance in said individual, comprising: administering to said individual a therapeutically effective amount of a composition comprising an estradiol metabolite selected from the group consisting of a catecholestradiol and a methoxyestradiol.

17. The method of claim 16, wherein said estradiol metabolite is selected from the group consisting of 2-hydroxyestradiol, 2-methoxyestradiol, 4-hydroxyestradiol and 4-methoxyestradiol.

18. The method of claim 16, wherein said composition comprises a controlled release formulation.

19. A method of treating an individual with pulmonary hypertension to decrease pulmonary vascular fibrosis in said individual, comprising: administering to said individual a therapeutically effective amount of a composition comprising an estradiol metabolite selected from the group consisting of a catecholestradiol and a methoxyestradiol.

20. The method of claim 19, wherein said estradiol metabolite is selected from the group consisting of 2-hydroxyestradiol, 2-methoxyestradiol, 4-hydroxyestradiol and 4-methoxyestradiol.

21. The method of claim 19, wherein said composition comprises a controlled release formulation.

22. A method of treating heart failure in an individuals comprising: administering to said individual a therapeutically effective amount of a composition comprising an estradiol metabolite selected from the group consisting of a catecholestradiol and a methoxyestradiol.

23. The method of claim 22, wherein said estradiol metabolite is selected from the group consisting of 2-hydroxyestradiol, 2-methoxyestradiol, 4-hydroxyestradiol and 4-methoxyestradiol.

24. The method of claim 22, wherein said composition comprises a controlled release formulation.

25. A method of treating an individual with pulmonary hypertension to reduce inflammation, cellular proliferation, vascular remodeling and vascular endothelial growth factor expression in the lungs, heart and pulmonary arteries of said individual, comprising: administering to said individual a therapeutically effective amount of a composition comprising an estradiol metabolite selected from the group consisting of a catecholestradiol and a methoxyestradiol.

26. The method of claim 25, wherein said estradiol metabolite is selected from the group consisting of 2-hydroxyestradiol, 2-methoxyestradiol, 4-hydroxyestradiol and 4-methoxyestradiol.

27. The method of claim 25, wherein said composition comprises a controlled release formulation.

* * * * *